United States Patent
Anderson et al.

(10) Patent No.: US 11,666,322 B2
(45) Date of Patent: Jun. 6, 2023

(54) METHOD OF FORMING A SUTURE-BUTTON-GRAFT COMBINATION AND FACILITATING CONSTRUCT

(71) Applicant: RIVERPOINT MEDICAL, LLC, Portland, OR (US)

(72) Inventors: Edwin Anderson, Ridgefield, WA (US); Elliot Bixby, Gladstone, OR (US); John Thomas Ferguson, Portland, OR (US)

(73) Assignee: Riverpoint Medical, LLC, Portland, OR (US)

( * ) Notice: Subject to any disclaimer, the term of this patent is extended or adjusted under 35 U.S.C. 154(b) by 275 days.

(21) Appl. No.: 17/185,253

(22) Filed: Feb. 25, 2021

(65) Prior Publication Data
US 2021/0259676 A1 Aug. 26, 2021

Related U.S. Application Data

(60) Provisional application No. 63/025,793, filed on May 15, 2020, provisional application No. 62/981,428, filed on Feb. 25, 2020.

(51) Int. Cl.
*A61B 17/04* (2006.01)
*A61B 17/06* (2006.01)
(Continued)

(52) U.S. Cl.
CPC .... *A61B 17/0401* (2013.01); *A61B 17/06066* (2013.01); *A61F 2/0811* (2013.01); *A61B 2017/00526* (2013.01); *A61B 2017/00867* (2013.01); *A61B 2017/0404* (2013.01); *A61B 2017/0414* (2013.01)

(58) Field of Classification Search
CPC .......... A61B 17/0401; A61B 17/06066; A61B 17/06166; A61B 2017/0404; A61B 2017/0414; A61B 2017/0406; A61B 2017/06057; A61B 2017/042; A61B 2017/044; A61B 2017/0459; A61B 2017/0485; A61B 2017/0409; A61B 2017/0475; A61F 2/0811
See application file for complete search history.

(56) References Cited

U.S. PATENT DOCUMENTS

| | | |
|---|---|---|
| 7,658,751 B2 | 2/2010 | Stone |
| 8,137,382 B2 | 3/2012 | Denham |

(Continued)

*Primary Examiner* — Tan-Uyen T Ho
*Assistant Examiner* — Regina Vahey
(74) *Attorney, Agent, or Firm* — Timothy E. Siegel Patent Law, PLLC; Timothy E. Siegel

(57) ABSTRACT

A suture and button construct, having an oblong button defining at least a first aperture and a second aperture; a suture length, including a braid defining a lumen and having a middle section and two end sections, each extending through a button aperture and both terminating in an end. Both ends have a needle attached. Also, two shuttles are engaged to the suture length, each having a free end and a loop end, terminating in a loop. Each shuttle enters the lumen in the middle section and extend through an aperture, while in the lumen and exit on the opposite button side from the middle section, so that both shuttle loops are available outside the lumen, to pull a suture end through the lumen and a button aperture.

20 Claims, 7 Drawing Sheets

(51) Int. Cl.
*A61F 2/08* (2006.01)
*A61B 17/00* (2006.01)

(56) References Cited

U.S. PATENT DOCUMENTS

| | | |
|---|---|---|
| 8,672,968 B2 | 3/2014 | Stone |
| 9,486,211 B2 | 11/2016 | Stone |
| 2013/0096612 A1* | 4/2013 | Zajac ................ A61B 17/0469 606/232 |

* cited by examiner

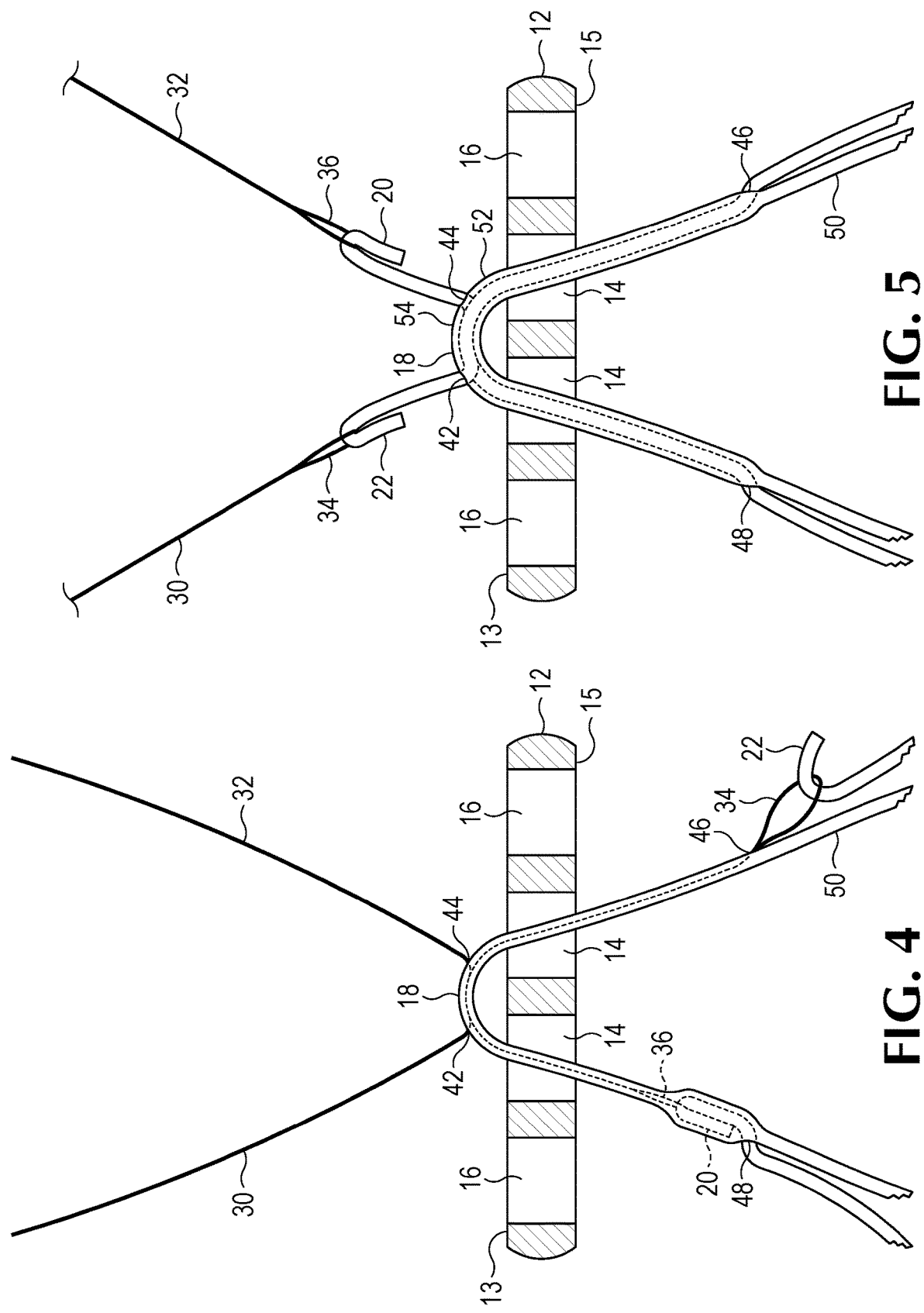

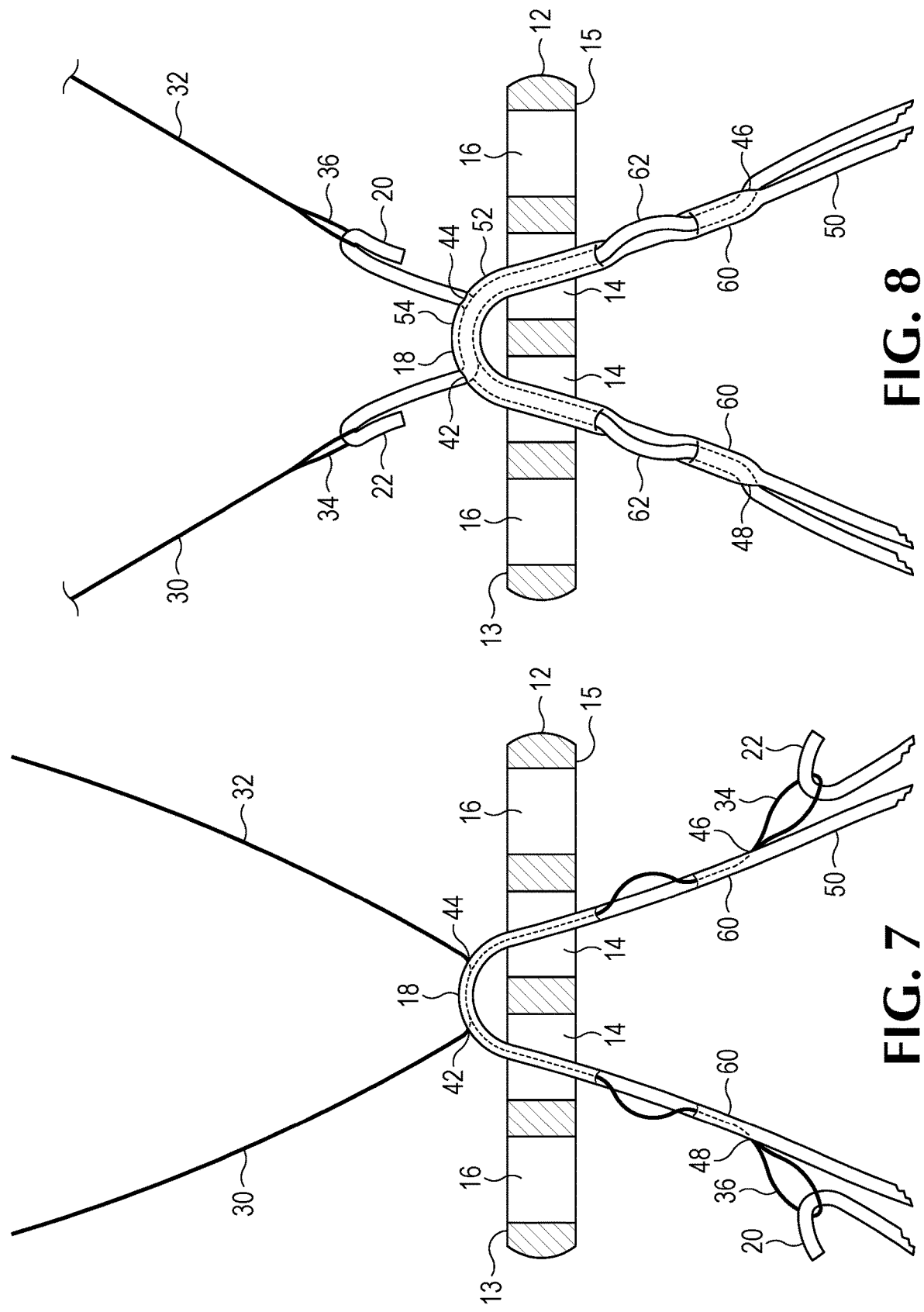

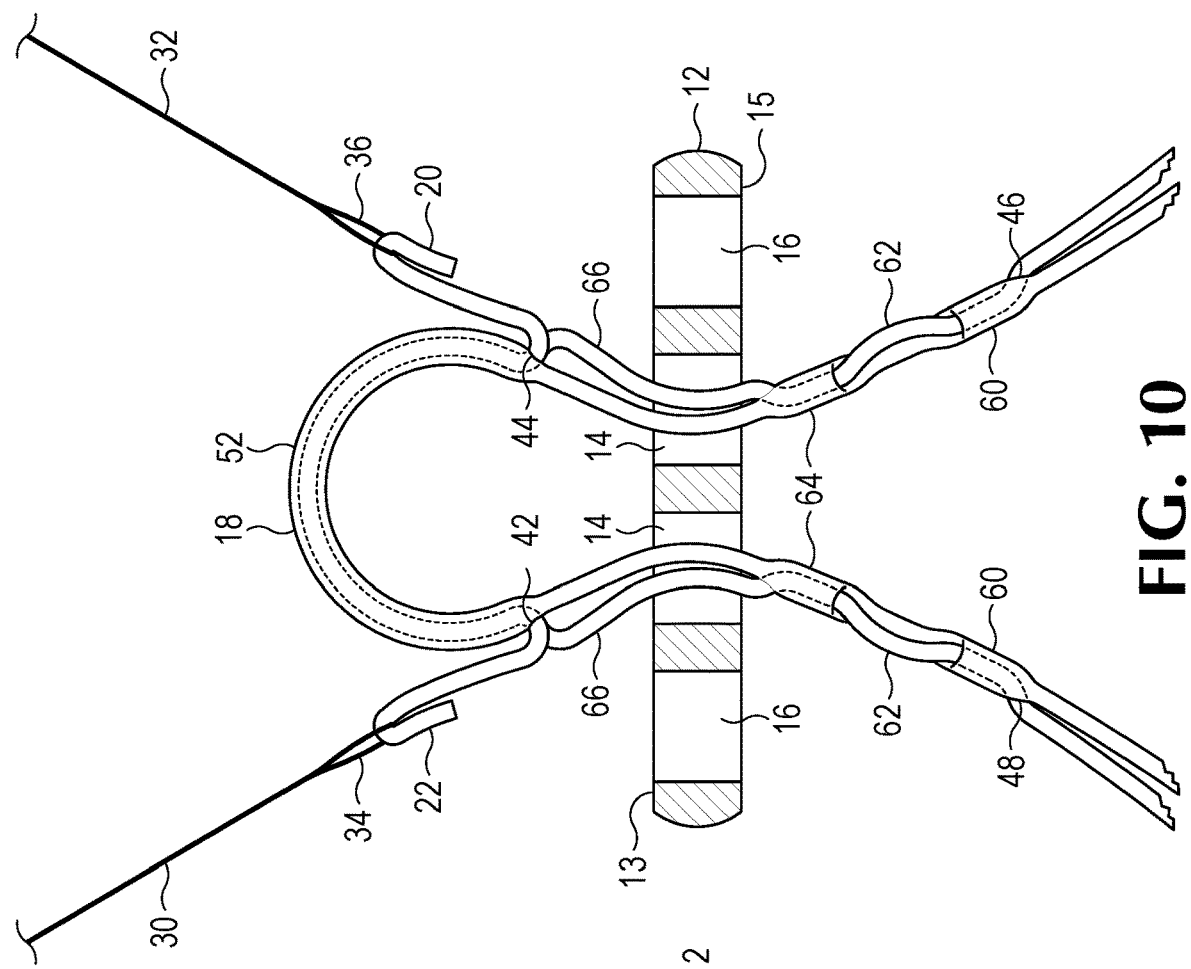
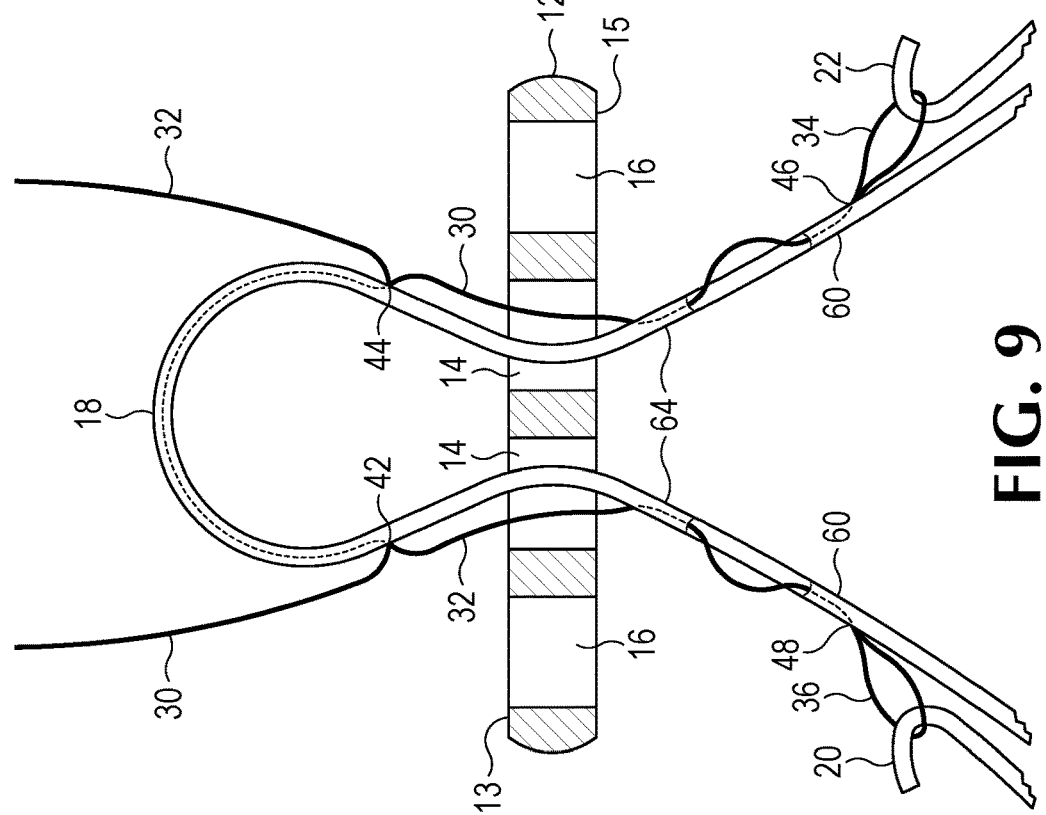

METHOD OF FORMING A SUTURE-BUTTON-GRAFT COMBINATION AND FACILITATING CONSTRUCT

This application is claims benefit of application U.S. Ser. No. 62/981,428, filed Feb. 25, 2020, and application U.S. Ser. No. 63/025,793, filed May 15, 2020, both of which are incorporated by reference as if fully set forth herein.

BACKGROUND OF THE INVENTION

Perhaps the most frequently performed tendon replacement surgery is the arthroscopic replacement of the anterior cruciform ligament ("ACL") in the knee of a patient. In this method a tunnel is drilled through the tibia and femur and a tendon graft is attached on either end to a suture construct and is introduced into the tunnel and positioned so that it abuts the tunnel interior surface so that it will gradually root into the tibia and femur. The suture construct on either side is attached to the cortical bone about the tunnel opening. In one method, the graft is attached on one or both ends to a suture construct that consists of a suture loop that is engaged to an oblong button. To introduce the graft into the tunnel, the button is passed through the tunnel, from the tibial to the femoral opening, and reoriented so that it rests on the cortical bone surface of the femur. There are advantages to performing the surgery in this manner, as a button resting on cortical bone is less disruptive to the patient than an anchor screw, engaged into the bone. In the case where the graft is harvested from the patient's hamstring, the graft may be draped over the bottom of the loop. Because of this, the button/loop construct may be purchased as a unit, with the graft being draped over and then trussed shortly before surgery. But in another technique, the graft is harvested from the patient's patella, which yields a graft that is comprised of bone on either end. Accordingly, this type of graft is generally referred to as a bone-tendon-bone ("BTB") graft. This type of graft is not long enough to be draped over the end of the loop in the same way as a hamstring graft. Consequently, until recently, a button/loop construct was not used with this type of graft, and other methods of fixation were used to attach the suture constructs, generally pierced through the ends of the graft to the ends of the tunnel. Recently, however, a method has been developed to construct the suture loop-button construct, attached to the graft, shortly before surgery. Another construct and method of constructing a suture-button-graft combination immediately before surgery would be beneficial to the medical community, by increasing available choices.

SUMMARY

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a method of constructing a button, suture loop and tendon graft combination that uses a tendon graft having a first end and a construct. The construct includes an oblong button that defines at least a first aperture and a second aperture and that has a first side and a second side; and a suture length, including a braid defining a lumen and having a middle section on the first side of the button and a first end section and a second end section, the first end section extending through the first aperture and the second end section extending through the second aperture, from the first side to the second side so that both the first end section and the second end section of the suture extend outwardly from the second side, the first end section terminating in a first end and the second end section terminating in a second end. The construct further includes a first needle attached to the first end and a second needle attached to the second end of the suture length; and a first and a second shuttle, each engaged to the suture length and each having a free end and a loop end, terminating in an end loop, the first shuttle enters the lumen in the middle section, at a first entrance point, and the second shuttle enters the lumen in the middle section at a second entrance point, the first shuttle extends though the first aperture, the loop end of the first shuttle extends out of the lumen at a first exit point and the loop end of the second shuttle extends out of the lumen at a second exit point. The method includes piercing the first end of the tendon graft with the first needle, in a first direction, and pulling the needle and a portion of the suture loop through the tendon graft and then piercing the first end of the tendon graft with the second needle, in a second direction opposed to the first direction, and pulling the second needle and a portion of the suture loop through the tendon graft. Then the needles are cut off, thereby leaving a first suture free end and a second suture free end and the first suture free end is engaged to the second shuttle end loop and pulling the second shuttle free end to pull the first suture free end through the lumen to exit from the lumen on the first side of the button and the second suture free end is engaged to the first shuttle end loop and pulling the first shuttle free end to pull the second suture free end through the lumen to exit from the lumen on the first side of the button.

In a second separate aspect, the present invention may take the form of a suture and button construct, having an oblong button defining at least a first aperture and a second aperture and having a first side and a second side; a suture length, including a braid defining a lumen and having a middle section on the first side of the button and a first end section and a second end section, the first end section extending through the first aperture and the second end section extending through the second aperture, from the first side to the second side so that both the first end section and the second end section of the suture extend outwardly from the second side, the first end section terminating in a first end and the second end section terminating in a second end; a first needle attached to the first end and a second needle attached to the second end of the suture length; and a first and a second shuttle, each engaged to the suture length and each having a free end and a loop end, terminating in a loop, the first shuttle entering the lumen in the middle section, at a first entry point, and the second shuttle entering the lumen in the middle section at a second entry point, the first shuttle extending though the first aperture together with the suture length and the second shuttle extending through the second aperture together with the suture length, the loop end of the first shuttle extending out of the lumen at a first exit point location and the loop end of the second shuttle extending out of the lumen at a second exit point.

BRIEF DESCRIPTION OF DRAWINGS

Various embodiments of the invention are disclosed in the following detailed description and accompanying drawings.

FIG. 4 is a detail view of the button portion of the construct of FIG. 1, in a further stage of configuration, from FIG. 3.

FIG. 5 is a detail view of the button portion of the construct of FIG. 1, in a further stage of configuration, from FIG. 4.

FIG. 7 is a detail view of the button portion of an alternative embodiment to the construct of FIG. 1, but which is the same in the portions not shown in FIG. 7, and which is in the same stage of deployment as the FIG. 1 configuration is in FIG. 4, except for that the end section has not been pulled into the lumen, yet.

FIG. 8 is a detail view of the button portion of FIG. 7, at a further stage of deployment.

FIG. 9 is a detail view of the button portion of another alternative embodiment to the construct of FIG. 1, but which is the same in the portions not shown in FIG. 7, and which is in the same stage of deployment as the FIG. 1 configuration is in FIG. 4, except for that the end section has not been pulled into the lumen, yet.

FIG. 10 is a detail view of the button portion of FIG. 9 at a further stage of deployment.

DETAILED DESCRIPTION AND EMBODIMENTS

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

Figure 1:
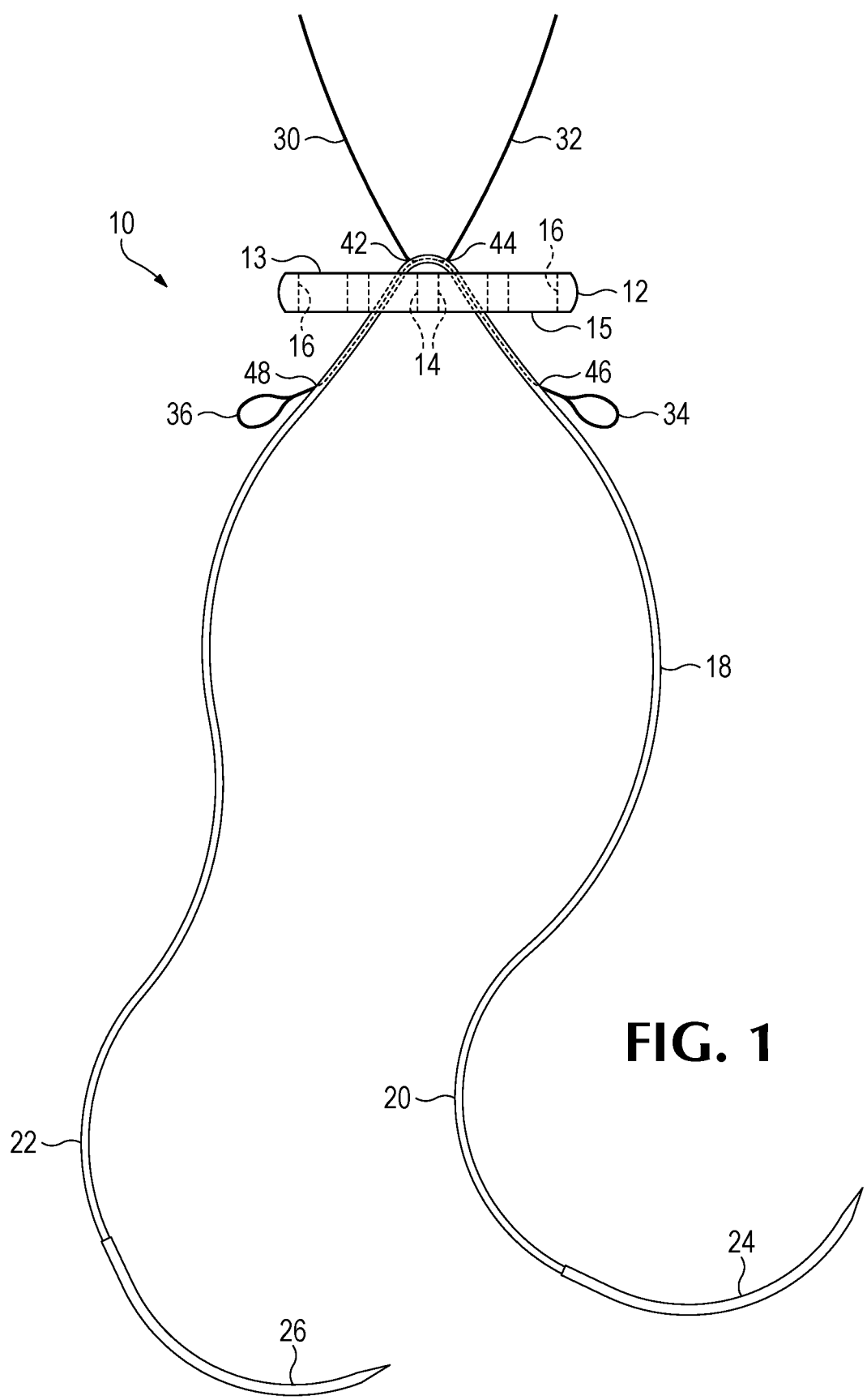
FIG. 1 is a front view of a suture/button construct, according to the present invention.

Referring to FIG. 1, a suture/button construct 10 includes an oblong button 12, having a first side (major surface) 13 and a second side 15 and also having a pair of inner apertures 14 and a pair of outer apertures 16. A suture length 18 is engaged to said inner apertures 14, so that on a first side of button 12 suture length 18 extends between the two inner apertures 14, on a second side of button 12, suture length 18 has two ends 20 and 22, as shown, each terminating into a needle 24 and 26, respectively. Suture length 18 is a circular braid that defines an inner lumen. A first shuttle 30 (which might also be referred to as a "tension member" having a terminal loop) and a second shuttle 32, each terminating in a terminal loop 34 and 36, respectively, enter at entrance points 42 and 44, respectively, extend through and exit, at exit point 46 and 48, respectively, from the inner lumen of suture length 18, crossing over each other in the process. Entrance points 42 and 44 are in a middle section of suture 18, which is on the first side of button 12 and are displaced from each other so that end sections 20 and 22 extend alongside each other inside the lumen.

Figure 2:
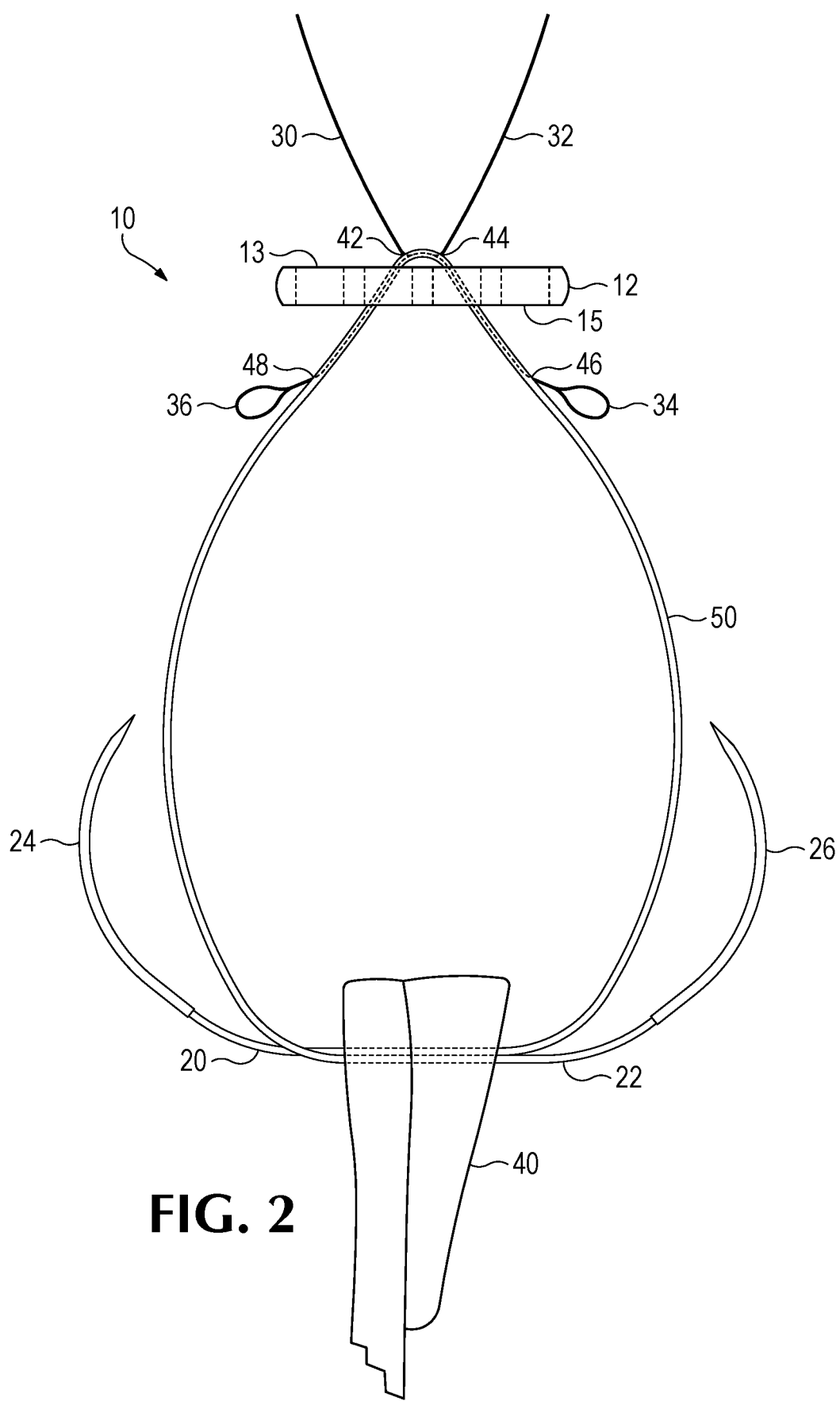
FIG. 2 is a front view of the suture/button construct of FIG. 1, engaged to a BTB graft.
Figure 3:
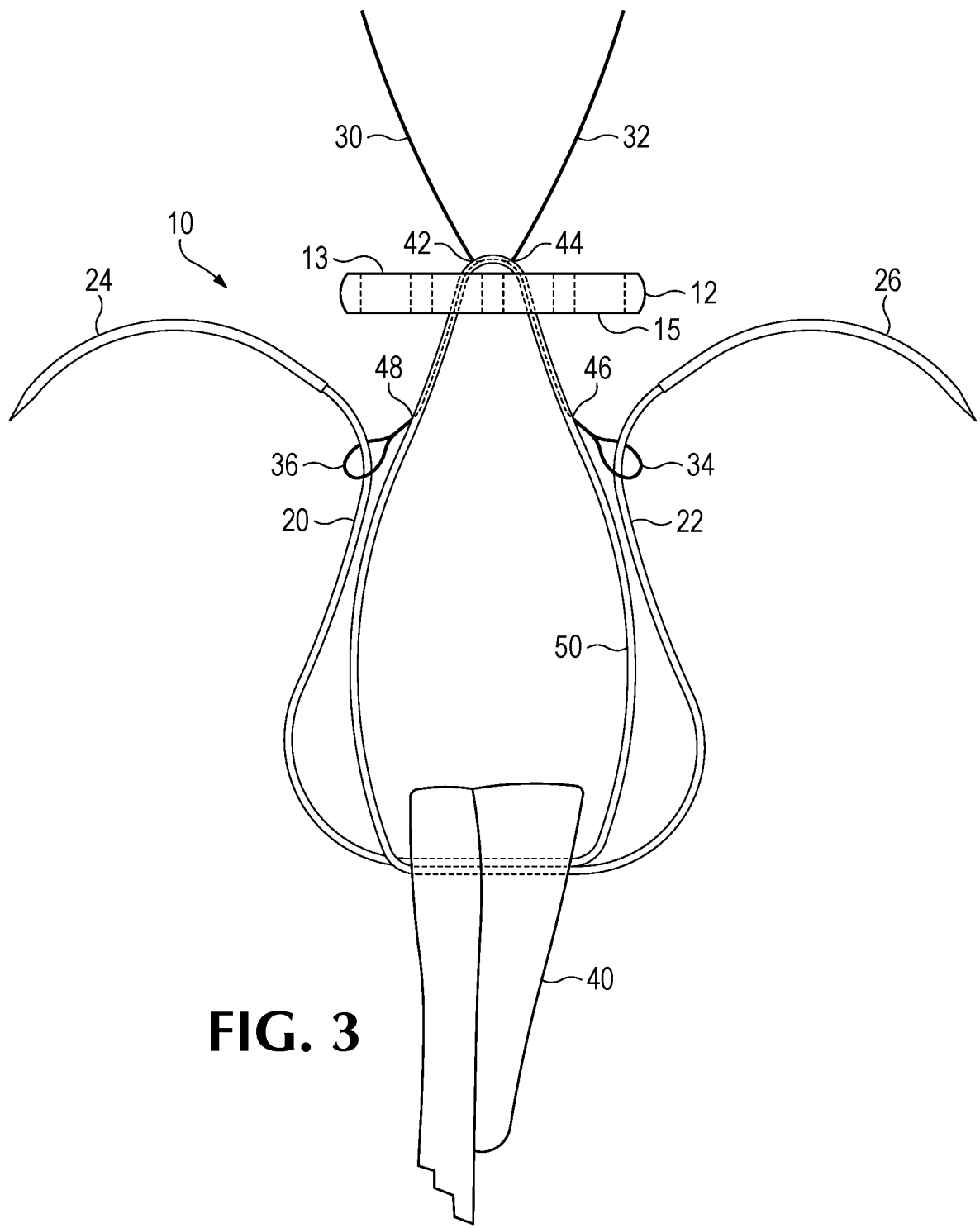
FIG. 3 is a front view of the suture/button construct of FIG. 1, engaged to a BTB graft, in a further stage of configuration from FIG. 2.
Figure 6:
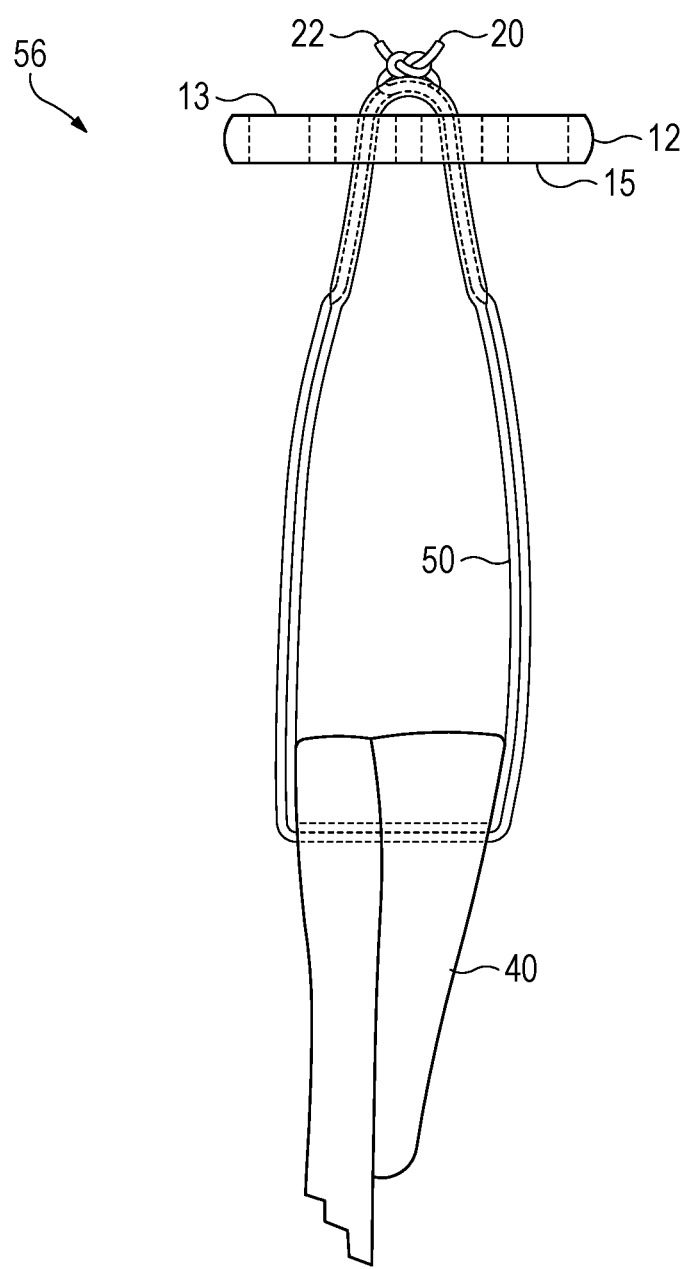
FIG. 6 is a front view of a completed button/suture/graft combination.

Referring now to FIG. 2, in a further step of constructing a button, suture loop and graft combination, a patella-harvested bone-tendon-bone graft 40 (only one end shown) has been pierced by needle 24 and needle 26, so that the two ends 20 and 22 extend through graft 40, thereby forming a loop 50. In the configuration shown in FIG. 3, needles 24 and 26 have been passed through terminal loops 36 and 34, respectively. In FIG. 4, needles 24 and 26 have been cut off the end sections 20 and 22, with end 20 shown as it has been pulled into the lumen of suture length 18. End 22 has been extended through loop 34 and is being pulled toward suture length 18. FIG. 5 shows the process when it is near the end result, with both ends 20 and 22 pulled through a portion of suture strand 18, to form a double trap 52 with a region of overlap 54. As shown in FIG. 6, this forms a construct 56 comprised of button 12, loop 50 and graft 40, with the graft suspended by the loop from the button. In the final stage, shuttles 30 and 32 have been removed and ends 20 and 22 are tied together, to ensure that the loop 50 does not lengthen over time. Alternatively, ends 20 and 22 are cut and/or permitted to retract into the lumen of suture length 18, where they are trapped by the inward pressure of the braid of length 18.

Either before or after the steps shown in FIGS. 2-5, the other end (not shown) of graft 40 is attached to some form of suture connection. At this point button 12 may be passed through the tunnel in the tibia and femur by pulling on a thread engaged through an outer aperture 16. Button 12 is then reoriented to sit on the cortical bone surface of the femur, thereby permitting graft 40 to extend in the tunnel, in an optimal position to grow into the tunnel walls of the femur and tibia. The other end of graft 40 is connected by a suture to the tibia opening of the tunnel, either by an anchor that may screw into the tibia, or in some instances, by the use of a button loop construct just like the one shown (in a close to final form) in FIG. 5.

FIGS. 7 and 8 illustrate an alternative embodiment in which shuttles 30 and 32 pull suture end sections 22 and 20 respectively, first into and out of shoulder trap regions 60 of suture length 18 to form a pair of shoulder traps at regions 60. Then shuttles 30 and 32 pull end sections 22 and 20 into a double trap portion 52 of suture length 18 and past each other to form a region of overlap 54. Expansion of loop 50, after implantation is a potential problem to be avoided, and introducing additional traps 60, and having an area of overlap of end sections 20 and 22, within double trap 52, helps to prevent this problem. In embodiments, this length of overlap is greater than 0.5, 1, 2 and 3 cm.

FIGS. 9 and 10 illustrate another alternative embodiment in which shuttle 30 enters double trap portion 52 of suture length 18 at the same place where shuttle 32 leaves portion 52, and shuttle 32 enters double trap portion 52 of suture length 18 at the same place where shuttle 30 leaves portion 52. Also, shuttles 30 and 32 pass through suture length 18 at shoulder trap regions 64 and 60. Accordingly, shuttles 30 and 32 pull suture end sections 22 and 20 respectively, first into and out of suture length 18 to form a first pair of shoulder traps at regions 60 and pass alongside suture 18 at free regions 62. Further members 30 and 32 pull end sections 22 and 20 into and out of suture length 18, to form another pair of shoulder traps at regions 64 and pass alongside suture length 18 at free regions 66, and then into and out of suture length 18, to form double trap 52, in which the two suture end sections 20 and 22 pass past each other for the entire length of trap 52, providing a greater retentive force to prevent the loop 50 from enlarging after implantation. In this embodiment, both the entry and exit points of shuttles 30 and 32 are on the first side 13 of button 12 so that they pass alongside suture length 18 as it passes through apertures 14, rather than inside the lumen of suture length 18 as in the previously discussed embodiments. In a further embodiment, trap regions 64 and free portions 62 are not present, so just traps 60 and trap 52 are in the final deployment. As may be well appreciated, this requires that both points 46 and 48 be located on the first side of button 12, with shuttles 30 and 32 passing through apertures 14 on the side of suture length 18. Expansion of loop 50, after implantation is a potential problem to be avoided, and introducing additional trap regions 64, and having an area of overlap of end sections 20 and 22, within double trap 52, helps to prevent this problem. In differing embodiments, this length of overlap is greater than 0.5, 1, 2, 3, 4 and 5 cm.

In one preferred embodiment, shuttles 30 and 32 are made of metal and more particularly nitinol. In one preferred embodiment, the interior of loops 34 and 36 is roughened, in a variant only at the bottom, to better engage and retain end sections 22 and 20, as they are folded over loops 34 and 36. In an embodiment an upward projection is created at the bottom of the interiors of loops 34 and 36 to positively engage with end sections 22 and 20. In a preferred embodiment, suture length 18 is made either in whole or in part of ultra-high molecular weight polyethylene.

The disclosed embodiments are illustrative, not restrictive. While specific configurations of the construct and method have been described, it is understood that the present invention can be applied to a wide variety of suture-button-graft configurations. There are many alternative ways of implementing the invention.

What is claimed is:

1. A method of constructing a button, suture loop and tendon graft combination, comprising:
   a) providing a tendon graft, having a first end;
   b) providing a construct having:
      i. an oblong button defining at least a first aperture and a second aperture and having a first side and a second side;
      ii. a suture length, including a braid defining a lumen and having a middle section on said first side of said button and a first end section and a second end section, said first end section extending through said first aperture and said second end section extending through said second aperture, from said first side to said second side so that both said first end section and said second end section of said suture extend outwardly from said second side, said first end section terminating in a first end and said second end section terminating in a second end;
      iii. a first needle attached to said first end and a second needle attached to said second end of said suture length; and
      iv. a first and a second shuttle, each engaged to said suture length and each having a free end and a loop end, terminating in an end loop, said first shuttle entering said lumen in said middle section, at a first entrance point, and said second shuttle entering said lumen in said middle section at a second entrance point, said first shuttle extending though said first aperture, said loop end of said first shuttle extending out of said lumen at a first exit point and said loop end of said second shuttle extending out of said lumen at a second exit point;
   c) piercing said first end of said tendon graft with said first needle, in a first direction, and pulling said needle and a portion of said suture loop through said tendon graft;
   d) piercing said first end of said tendon graft with said second needle, in a second direction opposed to said first direction, and pulling said second needle and a portion of said suture loop through said tendon graft;
   e) cutting off said needles, thereby leaving a first suture free end and a second suture free end;
   f) engaging said first suture free end to said second shuttle end loop and pulling said second shuttle free end to pull said first suture free end through said lumen to exit from said lumen on said first side of said button; and
   g) engaging said second suture free end to said first shuttle end loop and pulling said first shuttle free end to pull said second suture free end through said lumen to exit from said lumen on said first side of said button.

2. The method of claim 1, wherein said shuttles are made of metal.

3. The method of claim 2, wherein said shuttles are made of nitinol.

4. The method of claim 1, wherein said first entrance point and second entrance point are displaced from each other so that said first shuttle and second shuttle cross over each other within said lumen, in said middle section.

5. The method of claim 4, wherein said first shuttle and second shuttle extend side-by-side within the lumen for more than 2 mm.

6. The method of claim 1, wherein cutting off said needles is performed after engaging said suture free ends to said shuttle terminal loops.

7. The method of claim 1, wherein engaging said first suture free end and said second suture free end to their respective end loops is performed by folding said end sections over said terminal loops.

8. The method of claim 1, wherein said first and second exit points are on said first side of said button and said first and second shuttles extend through said first and second apertures aside said suture length.

9. The method of claim 1, wherein said first and second exit points are on said second side of said button and said first and second shuttles extend through said first and second aperture within said lumen.

10. The method of claim 1, wherein said first shuttle, as it extends from said first entrance point to said first exit point, exits and then enters said lumen thereby creating an additional trap.

11. The method of claim 10, wherein said second shuttle, as it extends from said second entrance point to said second exit point exits and then enters said lumen thereby creating another additional trap.

12. A suture and button construct, comprising:
   a) an oblong button defining at least a first aperture and a second aperture and having a first side and a second side;
   b) a suture length, including a braid defining a lumen and having a middle section on said first side of said button and a first end section and a second end section, said first end section extending through said first aperture and said second end section extending through said second aperture, from said first side to said second side so that both said first end section and said second end section of said suture extend outwardly from said second side, said first end section terminating in a first end and said second end section terminating in a second end;

c) a first needle attached to said first end and a second needle attached to said second end of said suture length; and d) a first and a second shuttle, each engaged to said suture length and each having a free end and a loop end, terminating in a loop, said first shuttle entering said lumen in said middle section, at a first entry point, and said second shuttle entering said lumen in said middle section at a second entry point, said first shuttle extending though said first aperture together with said suture length and said second shuttle extending through said second aperture together with said suture length, said loop end of said first shuttle extending out of said lumen at a first exit point location and said loop end of said second shuttle extending out of said lumen at a second exit point.

13. The suture and button construct of claim 12, wherein said shuttles are made of metal.

14. The suture and button construct of claim 13, wherein said shuttles are made of nitinol.

15. The suture and button construct of claim 12, wherein said first entrance point and second entrance point are displaced from each other so that said first shuttle and second shuttle cross over each other within said lumen, in said middle section.

16. The suture and button construct of claim 15, wherein said first shuttle and second shuttle extend side-by-side within the lumen for more than 5 mm.

17. The suture and button construct of claim 12, wherein said first shuttle extends out of said suture length at an additional exit point and back into said suture length at an additional entrance point.

18. The suture and button construct of claim 17, wherein said second shuttle extends out of said suture length at an additional exit point back into said suture length at an additional entrance point.

19. The suture and button construct of claim 12, wherein said first and second exit points are on said first side of said button and said first and second shuttles extend through said first and second apertures alongside said suture length.

20. The suture and button construct of claim 12, wherein said first and second exit points are of said second side of said button and said first and second shuttles extend through said first and second aperture within said lumen.

* * * * *